United States Patent [19]

Wirth et al.

[11] Patent Number: 4,814,167

[45] Date of Patent: Mar. 21, 1989

[54] PYRETTROID MACROEMULSIONS CONTAINING POLYVINYL ALCOHOL

[75] Inventors: Wolfgang Wirth, Hennef; Heinz J. Niessen; Bernd Klinksiek, both of Bergisch-Gladbach, all of Fed. Rep. of Germany

[73] Assignee: Bayer Aktiengesellschaft, Leverkusen, Fed. Rep. of Germany

[21] Appl. No.: 837,466

[22] Filed: Mar. 7, 1986

[30] Foreign Application Priority Data

Mar. 12, 1985 [DE] Fed. Rep. of Germany ....... 3508643
Apr. 11, 1985 [DE] Fed. Rep. of Germany ....... 3512917

[51] Int. Cl.$^4$ ..................... A61K 31/74; A01N 25/22; A01N 37/34
[52] U.S. Cl. ........................................ 424/78; 514/72; 514/73; 514/938; 252/312
[58] Field of Search ............... 252/312 AP S; 514/72, 514/73, 938; 424/78

[56] References Cited

U.S. PATENT DOCUMENTS

| | | | |
|---|---|---|---|
| 4,145,439 | 5/1979 | Schulze et al. | 514/471 |
| 4,303,640 | 12/1981 | Fuyama et al. | 424/78 |
| 4,372,943 | 2/1983 | Papanu et al. | 424/78 |
| 4,469,675 | 9/1984 | Curtis et al. | 514/531 |
| 4,500,348 | 2/1985 | Hausmann et al. | 71/103 |

FOREIGN PATENT DOCUMENTS

| | | |
|---|---|---|
| 1209361 | 8/1986 | Canada . |
| 1209362 | 8/1986 | Canada . |
| 0111580 | 6/1984 | European Pat. Off. . |
| 0148625 | 7/1985 | European Pat. Off. . |
| 2805251 | 8/1978 | Fed. Rep. of Germany . |
| 2924878 | 1/1980 | Fed. Rep. of Germany . |
| 2452249 | 10/1980 | France . |

*Primary Examiner*—John F. Terapane
*Assistant Examiner*—Gary Geist
*Attorney, Agent, or Firm*—Sprung Horn Kramer & Woods

[57] ABSTRACT

A macroemulsion which is stable to separation and crystallization over a wide range of temperature is disclosed. These macroemulsions contain:

0.0001 to 30% by weight of at least one solid pyrethroid,
0.0005 to 50% by weight of an aromatic diluent,
0.0001 to 15% by weight of polyvinyl alcohol having a mean molecular weight of between 5,000 and 60,000 and a content of acetate groups of between 2 and 30 mol %, if appropriate as a mixture with polyvinyl alcohol having a mean molecular weight of between 70,000 and 150,000 and a content of acetate groups of between 2 and 30 mol %, and water and acid and, if appropriate, further additives in which the oil phase is dispersed in the aqueous phase in the form of droplets having a mean particle diameter of 0.1 to 3.0 μm.

7 Claims, No Drawings

PYRETHROID MACROEMULSIONS CONTAINING POLYVINYL ALCOHOL

The present invention relates to new macroemulsions, a process for their preparation, and their use for combating pests.

A large number of aqueous emulsions of agrochemically active compounds has already been disclosed. Preparations of this type can be prepared, for example, by dissolving the generally water-insoluble active compounds in an amount of organic solvent, and adding an amount of emulsifier, such that sufficiently stable emulsions are formed when these formulations are diluted with water to the concentrations for use. However, the solvents present frequently give rise to concentrates having disadvantages because of the flammability, the toxicological properties, the toleration by plants and the odor.

In the case of active compounds which are not hydrolyzed by water when a particular pH is established, or which by their very nature are insensitive to hydrolysis, the organic solvents or mixtures of organic solvents may be partly or completely replaced with water in the preparation of plant protection formulations. When suitable emulsifiers are added, microemulsions are obtained, that is to say oil-in-water emulsions in which the oil phase is dispersed in the aqueous phase, in the form of droplets having a diameter of less than 0.1 $\mu$m (see EP-OS (European Published Specification) No. 0,062,181, EP-OS (European Published Specification) No. 0,107,009 and EP-OS (European Published Specification) No. 0,107,023). The disadvantage of these microemulsions is that the active compounds present are generally released very rapidly, with the result that the toxicity of the preparations, instead of being more advantageous, is thus frequently even less advantageous in the case of the concentrates in which larger amounts of organic solvents are present. Furthermore, microemulsion concentrates of this type are often stable to separation only in a narrow temperature range.

Macroemulsions of agrochemical active compounds are also known, that is to say oil-in-water emulsions in which the oil phase is dispersed in the aqueous phase in the form of droplets having a mean diameter of 1 to 200 $\mu$m. In the known macroemulsions, added thickeners are present for stabilization (see U.S. Pat. No. 4,303,640). However, because of the thickeners present, the viscosity of these macroemulsions is so high that volumetric metering of the preparations is made difficult, and substantial residual amounts of plant protection agents may remain in the emptied containers.

Finally, oil-in-water emulsions of certain agrochemical active compounds, which contain polyvinyl alcohol as a stabilizer in addition to conventional emulsifiers, are also known (see EP-OS (European Published Specification) No. 0,111,580). However, the toxicological properties of emulsions of this type, which have a mean particle size of < 1 $\mu$m, are less advantageous than those of corresponding emulsions in which only polyvinyl alcohol is present as a stabilizer. In particular, an undesired irritating effect on the skin and on the mucous membranes occurs in some cases during application of the spray liquors diluted to the concentration for use.

The present invention relates to new macroemulsions which contain 0.0001 to 30% by weight of at least one solid pyrethroid, 0.0005 to 50% by weight of an aromatic diluent, 0.0001 to 15% by weight of polyvinyl alcohol having a mean molecular weight of between 5,000 and 60,000 and a content of acetate groups of between 2 and 30 mol%, if appropriate as a mixture with polyvinyl alcohol having a mean molecular weight of between 70,000 and 150,000 and a content of acetate groups of between 2 and 30 mol%, and water and acid and, if appropriate, further additives and in which the oil phase is dispersed in the aqueous phase in the form of droplets having a mean particle diameter of 0.1 to 3.0 $\mu$m.

Furthermore, it has been found that the macroemulsions according to the invention can be prepared by a process in which an aqueous solution which contains between 1 and 25% by weight of polyvinyl alcohol having a mean molecular weight of between 5,000 and 60,000 and a content of acetate groups of between 2 and 30 mol%, and, if appropriate, an aqueous solution which contains between 1 and 15% by weight of polyvinyl alcohol having a mean molecular weight of between 70,000 and 150,000 and a content of acetate groups of between 2 and 30 mol%, are added to a solution of at least one solid pyrethroid in an aromatic diluent at temperatures between 10° and 30° C., the resulting emulsion, if appropriate after additives have been introduced beforehand, is then homogenized at temperatures between 10° and 70° C. by means of a suitable apparatus, and acid and, if appropriate, further additives are then added and the emulsion is made up to the desired concentration with water.

Finally, it has been found that the macroemulsions according to the invention are very suitable for combating pests.

It must be regarded as extremely surprising that the macroemulsions according to the invention have a less irritating effect on skin and mucous membranes than corresponding previously known emulsions which contain organic solvents and conventional emulsifiers. The fact that the formulations according to the invention are stable, over a relatively wide temperature range, in regard to degradation of the active compound, crystallization of the active compound and separation is also unexpected.

The macroemulsions according to the invention are also distinguished by a number of advantages. Thus, they can be prepared in a simple manner using readily available auxiliaries. The addition of thickeners and emulsifiers is not necessary. Furthermore, the macroemulsions according to the invention have a low viscosity, so that volumetric metering can be carried out without difficulties. Moreover, the advantageous toxicological properties, and the good dispersibility in water and the good physical stability of the emulsions according to the invention both at low temperatures and at high temperatures should also be singled out.

The macroemulsions according to the invention contain, as active components, one or more insecticidal and/or acaricidal substances which are solid at room temperature and belong to the class comprising the pyrethroids. In this context, solid active compounds are also understood as meaning those components which are semi-crystalline at room temperature. $\alpha$-Cyano-3'-phenoxy-4'-fluorobenzyl 2,2-dimethyl-3-($\beta$,$\beta$-dichlorovinyl)-cis/trans-cyclopropanecarboxylate and 2,3,4,5,6-pentafluorobenzyl 3-(2,2-dichlorovinyl)-2,2-dimethyl-cyclopropanecarboxylate may be mentioned as examples.

All customary aromatic solvents or solvent mixtures which boil between 100° C. and 290° C. may be present in the macroemulsions according to the invention. Toluene, ethylbenzene, chlorobenzene, xylenes, alkylated benzenes having an average of 9 carbon atoms, such as the solvent types known under the name Solvesso ®, and naphthlene which is optionally substituted by alkyl having 1 to 3 carbon atoms are preferred.

The macroemulsions according to the invention contain polyvinyl alcohol having a mean molecular weight of between 5,000 and 60,000, preferably between 20,000 and 50,000, and a content of acetate groups of between 2 and 30 mol%, and, if appropriate, polyvinyl alcohol having a mean molecular weight of between 70,000 and 150,000, preferably between 80,000 and 125,000, and a content of acetate groups of between 2 and 30 mol%.

The following may be mentioned as examples of polyvinyl alcohols of this type: polyvinyl alcohol having a mean molecular weight of 47,000 and a content of acetate groups of 12 mol%, polyvinyl alcohol having a mean molecular weight of 99,000 and a content of acetate groups of 12 mol%, polyvinyl alcohol having a mean molecular weight of 81,000 and a content of acetate groups of 12 mol%, and polyvinyl alcohol having a mean molecular weight of 25,000 and a content of acetate groups of 12 mol%, polyvinyl alcohol having a mean molecular weight of 82,000 and a content of acetate groups of 17 mol%, polyvinyl alcohol having a means molecular weight of 85,000 and a content of acetate groups of 23 mol%, polyvinyl alcohol having a mean molecular weight of 27,000 and a content of acetate groups of 29 mol% and polyvinyl alcohol having a mean molecular weight of 75,000 and a content of acetate groups of 4 mol%.

In each case, the content of acetate groups constitutes a measure of the degree of hydrolysis of the polyvinyl alcohol prepared from polyvinyl acetate.

Acids which are present in the macroemulsions according to the invention can be inorganic and organic acids. Phosphoric acid, citric acid and benzoic acid may be mentioned as examples.

Additives which may be present in the macroemulsions according to the invention can be dyestuffs, preservatives, antifoams, antifreezes, crystallization inhibitors and odor improvers.

In this context, anthraquinone dyestuffs, azo dyestuffs and phthalocyanine dyestuffs may be mentioned as examples of dyestuffs.

2-Hydroxybiphenyl, sorbic acid, p-hydroxybenzaldehyde, methyl p-hydroxybenzoate, benzaldehyde, benzoic acid, propyl p-hydroxybenzoate, p-nitrophenol and the preservative on the market under the name Preventol ® and Dimamin ® may be mentioned as examples of preservatives.

Suitable antifoams are silicone oils.

Glycerol, glycol, urea, sugar and polyethylene glycol may be mentioned as examples of antifreezes.

Examples of crystallization inhibitors are alkylphenols which are condensed with 1 to 8 moles of ethylene oxide per mol. Nonylphenol which has been condensed with 2 moles of ethylene oxide per mol may be mentioned in particular in this context.

Perfume oils may be employed as odor improvers.

The macroemulsions according to the invention contain water as the continuous phase. In the case of concentrates, the amount of water is relatively small. In the case of highly dilute emulsions, substantial amounts of water are present.

In the macroemulsions according to the invention, the oil phase (=disperse phase) is dispersed in the aqueous phase in the form of droplets. The size of the oil droplets can be varied within a certain range. In general, the mean particle diameter is between 0.1 and 3 $\mu$m, preferably between 0.4 and 2.5 $\mu$m.

In the macroemulsions according to the invention, the percentages of the components present may be varied within wide ranges. The amount of pyrethroid is in general between 0.0001 and 30% by weight, preferably between 0.001 and 20% by weight. The amount of aromatic diluent is in general between 0.0005 and 50% by weight, preferably between 0.005 and 40% by weight, and the amount of polyvinyl alcohol is in general between 0.0001 and 15% by weight, preferably between 0.001 and 10% by weight. Acids are present in general in amounts of 0.0001 to 0.5% by weight, preferably from 0.001 to 0.1% by weight. Additives may be present, if required, in amounts of between 0.01 and 15% by weight, preferably between 0.1 and 10% by weight. The percentage of water in the macroemulsions according to the invention is in each case the difference between 100% by weight and the sum of the percentages of the other components.

In the preparation of the macroemulsions according to the invention, it is preferable to use all those components which have already been mentioned in connection with the description of the macroemulsions according to the invention as being preferred or by way of example.

In carrying out the process according to the invention, polyvinyl alcohol is generally employed in the form of aqueous solutions. The concentrations of these solutions can be varied within a certain range. In general, aqueous solutions which contain between 0.1 and 30% by weight, preferably between 1 and 25% by weight, of polyvinyl alcohol are used.

The reaction temperatures can be varied within a certain range, both in the first and in the second stage of the process according to the invention. The first stage is generally carried out at temperatures between 10° and 30° C., preferably between 15° and 25° C. The second stage is generally carried out at temperatures between 10° and 70° C., preferably between 15° and 65° C.

Homogenization in the second stage of the process according to the invention is preferably carried out using high-pressure homogenizers or jet dispersers. Jet dispersers in which the pressure drop per dispersing nozzle is between 10 and 50 bar are preferably employed. Jet dispersers of this type are already known (see EP-OS (European Published Specification) No. 0,101,007).

In carrying out the process according to the invention, the following procedure is generally adopted:

in the first stage, one or more aqueous polyvinyl alcohol solutions and, if appropriate, additives are added to a stirred solution of at least one solid pyrethroid in an aromatic diluent at temperatures between 10° C. and 30° C., then, in a second stage, the resulting pre-emulsion is homogenized at temperatures between 10° C. and 70° C. and with the aid of a suitable apparatus, and acid and, if appropriate, further additives are then added, and the emulsion is made up to the desired concentration with water.

The amounts of the components are chosen so that macroemulsions are formed in which the concentrations of the individual constituents are in the ranges stated above.

The macroemulsions according to the invention possess very good insecticidal and acaricidal properties. They can therefore be employed for combating insects and arachnida in agriculture, in horticulture and in the household and hygiene sectors, as well as in the veterinary sector.

The macroemulsions according to the invention can be applied either in the prepared form or after being diluted beforehand. The amount used depends on the concentration of the active compounds in the formulation and on the particular indication.

The macroemulsions according to the invention are applied, if appropriate after being diluted beforehand, by customary methods, that is to say, for example, by spraying, atomizing or watering.

The preparation of the macroemulsions according to the invention is illustrated by the Examples which follow.

PREPARATION EXAMPLES

Example 1

5 parts by weight of α-cyano-3'-phenoxy-4'-fluoro-benzyl 2,2-dimethyl-3-(β,β-dichlorovinyl)-cis/trans-cyclopropanecarboxylate are dissolved in 9 parts by weight of an aromatic solvent known under the name Solvesso 100 ®. 32 parts by weight of a 10% strength by weight aqueous solution of a polyvinyl alcohol having a mean molecular weight of 47,000 and a content of acetate groups of 12 mol% and 8 parts by weight of a 10% strength by weight aqueous solution of a polyvinyl alcohol having a mean molecular weight of 99,000 and a content of acetate groups of 12 mol% are added to the solution at room temperature and while stirring gently. The resulting pre-emulsion is homogenized at room temperature using a jet disperser in which the pressure drop per dispersing nozzle is 40 bar. Thereafter, the dispersion is made up to 100 parts by weight with demineralized water and 40% strength by weight aqueous citric acid so that the pH value of the emulsion is 3.5. A macroemulsion in which the oil phase is dispersed in the aqueous phase in the form of droplets having a mean particle diameter of 1.3 μm is obtained in this manner.

The macroemulsion obtained remained stable even after storage for 8 weeks in a thermal cycling chamber at temperatures between −15° C. and +30° C., and at +50° C.

Example 2

The macroemulsion described in Example 1 is diluted by further addition of water and 40% strength by weight aqueous citric acid so that a macroemulsion is formed in which the pH value is 3.5 and 0.015 parts by weight of α-cyano-3'-phenoxy-4'-fluorobenzyl 2,2-dimethyl-3-(β,β-dichlorovinyl)-cis/trans-cyclopropanecarboxylate are present.

The macroemulsion thus obtained remained stable even after storage for 8 weeks in a thermal cycling chamber at temperatures between −15° C. and +30° C., and at +50° C.

Example 3

1.66 parts by weight of α-cyano-3'-phenoxy-4'-fluorobenzyl 2,2-dimethyl-3-(β,β-dichlorovinyl)-cis/-trans-cyclopropanecarboxylate and 3.33 parts by weight of 2,3,4,5,6-pentafluorobenzyl 3-(2,2-dichlorovinyl)-2,2-dimethylcyclopropanecarboxylate are dissolved in 11 parts by weight of an aromatic solvent known under the name Solvesso 100 ®. 77.2 parts by weight of a 10% strength by weight aqueous solution of a polyvinyl alcohol having a mean molecular weight of 47,000 and a content of acetate groups of 12 mol% are added to the solution at room temperature and while stirring gently. The resulting pre-emulsion is heated to 50° C. and homogenized using a jet disperser in which the pressure drop per dispersing nozzle is 40 bar. The emulsion is then made up to 100 parts by weight with demineralized water and 40% strength by weight aqueous ciric acid so that the pH value of the emulsion is 3.5. A macroemulsion in which the oil phase is dispersed in the aqueous phase in the form of droplets having a mean particle diameter of 1.1 μm is obtained in this manner.

The macroemulsion obtained remained stable even after storage for 8 weeks in a thermal cycling chamber at temperatures between −15° C. and +30° C., and at +50° C.

It will be understood that the specification and examples are illustrative but not limitative of the present invention and that other embodiments within the spirit and scope of the invention will suggest themselves to those skilled in the art.

What is claimed is:

1. A macroemulsion consisting essentially of 0.0001 to 30% by weight of
   at least one solid pyrethroid,
   0.0005 to 50% by weight of an aromatic diluent
   0.0001 to 15% by weight of polyvinyl alcohol having a mean molecular weight of between 5,000 and 60,000 and a content of acetate groups of between 2 and 30 mol%, or a mixture of said polyvinyl alcohol with polyvinyl alcohol having a mean molecular weight of between 70,000 and 150,000 and a content of acetate groups of between 2 and 30 mol%,
   and water and acid selected from the group consisting of phosphoric acid, citric acid, and benzoic acid,
   wherein
   the oil phase of said macroemulsion is dispersed in the aqueous phase of said emulsion in the form of droplets having a mean particle diameter of between 0.1 and 3.0 μm.

2. A macroemulsion according to claim 1, wherein said solid pyrethroid is selected from the group consisting of
   α-cyano-3'-phenoxy-4'-fluoro-benzyl 2,2-dimethyl-3-(β,β-dichlorovinyl)-cis/trans-cyclopropanecarboxylate and/or 2,3,4,5,6-pentafluorobenzyl-3-(2,2-dichlorovinyl)-2,2-dimethyl-cyclopropanecarboxylate.

3. A macroemulsion according to claim 1, wherein toluene, ethylbenzene, cholorbenzene, xylenes, alkylated benzenes having an average of 9 carbon atoms and/or naphthalene which is optionally substituted by alkyl having 1 to 3 carbon atoms is present as said aromatic diluent.

4. A macroemulsion according to claim 1, wherein said polyvinyl alcohol is a polyvinyl alcohol having a mean molecular weight of between 20,000 and 50,000 and a content of acetate groups of 2 to 30 mol% or a mixture of said polyvinyl alcohol with polyvinyl alcohol having a mean molecular weight of between 80,000 and 125,000 and a content of acetate groups of 2 to 30 mol%.

5. A macroemulsion according to claim 1, wherein said macroemulsion comprises further additives selected from the group consisting of dyestuffs, preservative, antifoams, antifreezes, crystallization inhibitors and odor improvers.

6. A macroemulsion according to claim 1, wherein the oil phase is dispersed in the aqueous phase in the form of droplets having a mean particle diameter of between 0.4 μm and 2.5 μm.

7. A method of combating pests comprising applying to said pests or a habitat thereof the macroemulsion according to claim 1.

* * * * *